United States Patent
Battle et al.

(10) Patent No.: US 10,083,518 B2
(45) Date of Patent: Sep. 25, 2018

(54) DETERMINING A BIOPSY POSITION

(71) Applicant: Siemens Healthcare GmbH, Erlangen (DE)

(72) Inventors: Xavier Battle, Forchheim (DE); Rainer Grimmer, Erlangen (DE); Philipp Hoelzer, Bubenreuth (DE); Bernhard Schmidt, Fuerth (DE); Grzegorz Soza, Heroldsberg (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 15/904,658

(22) Filed: Feb. 26, 2018

(65) Prior Publication Data
US 2018/0247415 A1    Aug. 30, 2018

(30) Foreign Application Priority Data
Feb. 28, 2017  (DE) .......................... 10 2017 203 248

(51) Int. Cl.
*G06K 9/62* (2006.01)
*G06T 7/12* (2017.01)
(Continued)

(52) U.S. Cl.
CPC .............. *G06T 7/12* (2017.01); *A61B 6/482* (2013.01); *A61B 6/5235* (2013.01); *A61B 34/10* (2016.02);
(Continued)

(58) Field of Classification Search
None
See application file for complete search history.

(56) References Cited

U.S. PATENT DOCUMENTS

| 5,989,811 A * | 11/1999 | Veltri | G01N 33/574 435/6.14 |
| 6,025,128 A * | 2/2000 | Veltri | C12Q 1/68 435/6.14 |

(Continued)

OTHER PUBLICATIONS

German Office Action #102017203248.0 dated Nov. 15, 2017.
German Decision to Grant a Patent #102017203248.0 dated Nov. 29, 2017.

*Primary Examiner* — Jayesh A Patel
(74) *Attorney, Agent, or Firm* — Harness, Dickey & Pierce, P.L.C.

(57) ABSTRACT

A method includes receiving an image data set of an examination volume including a tumor. A tumor region is segmented in the image data set. Furthermore, a texture distribution of the tumor region is determined, the texture distribution in each case assigning a texture parameter to image points in the tumor region, and each of the texture parameters being based on a spatial distribution of first intensity values of the image data set. Furthermore, a biopsy position within the tumor region is determined by applying an optimized position-determining algorithm to the texture distribution, the optimized position-determining algorithm being based on training texture distributions and first training positions, and one of the first training positions being assigned to each of the training texture distributions. In embodiments, the use of an optimized position-determining algorithm enables all relevant influencing variables for the determination of the biopsy position to be taken into account.

28 Claims, 4 Drawing Sheets

(51) Int. Cl.
  *G06T 7/40* (2017.01)
  *A61B 6/00* (2006.01)
  *A61B 34/10* (2016.01)
  *A61B 6/03* (2006.01)

(52) U.S. Cl.
  CPC ............... *G06T 7/40* (2013.01); *A61B 6/03* (2013.01); *A61B 6/037* (2013.01); *A61B 2034/107* (2016.02); *G06T 2207/10104* (2013.01); *G06T 2207/20081* (2013.01); *G06T 2207/20084* (2013.01); *G06T 2207/30096* (2013.01)

(56) References Cited

U.S. PATENT DOCUMENTS

| | | | | |
|---|---|---|---|---|
| 6,026,174 | A * | 2/2000 | Palcic | G01N 1/30 382/128 |
| 6,081,612 | A * | 6/2000 | Gutkowicz-Krusin | A61B 5/0071 382/128 |
| 6,208,749 | B1 * | 3/2001 | Gutkowicz-Krusin | A61B 5/442 382/128 |
| 7,556,602 | B2 * | 7/2009 | Wang | A61B 6/463 382/128 |
| 8,295,575 | B2 * | 10/2012 | Feldman | G06K 9/6252 382/131 |
| 8,488,863 | B2 * | 7/2013 | Boucheron | G06K 9/0014 382/131 |
| 8,655,035 | B2 * | 2/2014 | Malon | G06K 9/00 382/128 |
| 2001/0031076 | A1 * | 10/2001 | Campanini | G06K 9/3233 382/128 |
| 2002/0045153 | A1 * | 4/2002 | Kaufman | G06K 9/209 434/262 |
| 2003/0065260 | A1 * | 4/2003 | Cheng | A61B 8/0833 600/427 |
| 2005/0162419 | A1 * | 7/2005 | Kim | G06T 15/00 345/419 |
| 2006/0204071 | A1 * | 9/2006 | Ortyn | G01J 3/2889 382/133 |
| 2006/0247862 | A1 * | 11/2006 | Arini | G06K 9/00127 702/19 |
| 2008/0170770 | A1 * | 7/2008 | Suri | A61B 8/12 382/128 |
| 2008/0292194 | A1 * | 11/2008 | Schmidt | G06T 7/0012 382/217 |
| 2008/0304733 | A1 * | 12/2008 | Macaulay | G01N 33/5091 382/133 |
| 2009/0154781 | A1 * | 6/2009 | Bogdan | G06T 7/0012 382/128 |
| 2010/0111396 | A1 * | 5/2010 | Boucheron | G06K 9/0014 382/133 |
| 2010/0142775 | A1 * | 6/2010 | Ganeshan | G06K 9/4609 382/128 |
| 2010/0329529 | A1 * | 12/2010 | Feldman | G06K 9/6252 382/131 |
| 2011/0293165 | A1 * | 12/2011 | Malon | G06K 9/00 382/133 |
| 2012/0197657 | A1 * | 8/2012 | Prodanovic | G06Q 50/22 705/2 |
| 2015/0018666 | A1 * | 1/2015 | Madabhushi | A61B 8/12 600/411 |
| 2015/0206022 | A1 * | 7/2015 | Radha Krishna Rao | G06K 9/4604 382/128 |
| 2017/0103525 | A1 * | 4/2017 | Hu | G06T 7/0012 |

* cited by examiner

DETERMINING A BIOPSY POSITION

PRIORITY STATEMENT

The present application hereby claims priority under 35 U.S.C. § 119 to German patent application number DE 102017203248.0 filed Feb. 28, 2017, the entire contents of which are hereby incorporated herein by reference.

FIELD

At least one embodiment of the invention is generally directed to determining a biopsy position.

BACKGROUND

The removal of specimens by way of a biopsy is a known and widely used method for evaluating the condition of a part of the human body. In particular in the case of tumor diseases, the specimens removed can be used as the basis for the evaluation of the progression of the tumor disease and the determination of suitable therapeutic measures.

Tumors are typically heterogeneous; in particular, there are regions in the tumor with a high degree of activity and/or growth (high malignancy) and regions with a low degree of activity and/or growth (low malignancy). In order to assess the type and stage of the tumor disease correctly based on a removed specimen, the specimen should be removed from a region with high activity and/or growth.

It is known to use medical imaging to determine the position and extent of a tumor in the human body and to remove the biopsy at a random position or a position within the tumor determined based on the geometry of the tumor. However, herein, it is also possible that the specimen will be removed randomly from a region with a low degree of activity and/or growth and that the evaluation of the specimen will produce false conclusions.

Furthermore, it is known to remove several specimens from different regions of the tumor and to use the specimen indicative of the highest degree of activity and/or growth as the specimen for the evaluation of the tumor disease. However, the removal and analysis of numerous specimens is time-consuming and expensive and multiple removal represents a higher risk to the health of patient than one single removal.

SUMMARY

At least one embodiment of the present invention provides a method for determining a biopsy position in a region with high activity and/or growth based on medical imaging. Herein, a biopsy position is a planned position at the location of which a biopsy is to be removed.

At least one embodiment of the present invention is directed to a method for determining a biopsy position; at least one embodiment of the present invention is directed to a method for optimizing a position-determining algorithm; at least one embodiment of the present invention is directed to a position-determining unit; at least one embodiment of the present invention is directed to an imaging medical device; at least one embodiment of the present invention is directed to a computer-program product; and at least one embodiment of the present invention is directed to a computer-readable storage medium.

Features, advantages or alternative embodiments mentioned herein may also be transferred to the other claimed subject matter and vice versa. In other words, the substantive claims (which are, for example, directed at a device) can also be developed with the features described or claimed in connection with a method. Herein, the corresponding functional features of the method are embodied by corresponding substantive modules.

Furthermore, the following describes solutions according to embodiments of the invention with respect to both methods and devices for determining a biopsy position and with respect to methods and devices for optimizing a position-determining algorithm. Features, advantages or alternative embodiments mentioned herein may also be transferred to the other claimed devices and methods and vice versa. In other words, claims for methods and devices for determining a biopsy position can also be developed with features described or claimed in connection with methods and devices for optimizing a position-determining algorithm. In particular, the described advantages of developments of embodiments of the method and the device for determining a biopsy position can be transferred to advantages of the developments of embodiments of the method and the device for optimizing a position-determining algorithm and vice versa.

At least one embodiment of the present invention is directed to a method where an image data set of an examination volume is received via an interface, wherein the examination volume includes a tumor. Furthermore, a tumor region is segmented in the image data set via a computing unit. Furthermore, a texture distribution of the tumor region is determined via the computing unit, wherein the texture distribution in each case assigns a texture parameter to image points in the tumor region, wherein each of the texture parameters is based on a spatial distribution of first intensity values of the image data set. Furthermore, a biopsy position within the tumor region is determined by applying an optimized position-determining algorithm to the texture distribution via the computing unit, wherein the optimized position-determining algorithm is based on training texture distributions and first training positions, wherein one of the first training positions is assigned to each of the training texture distributions.

The method according to an embodiment of the invention for optimizing a position-determining algorithm is based on the principle that a first training image data set and a second training image data set of a training tumor region is received via a training interface. Furthermore, a training computing unit determines a training texture distribution of the training tumor region, wherein the training texture distribution in each case assigns a training texture parameter to first training image points of the first training image data set and wherein each of the training texture parameters is based on a spatial distribution of first training intensity values of the first training image data set.

Furthermore, based on a growth rate in the training tumor region, a first training position is determined via the training computing unit, wherein the growth rate is based on the second training image data set. Furthermore, the training interface receives a position-determining algorithm, wherein the position-determining algorithm is based on a plurality of algorithm parameters. Furthermore, the training computing unit determines a second training position by applying the position-determining algorithm to the training texture distribution. Furthermore, the training computing unit optimizes a position-determining algorithm by adjusting the algorithm parameters based on a comparison of the first training position with the second training position. Herein, a position-determining algorithm can in particular be an artificial intelligence system.

An embodiment of the invention furthermore relates to a position-determining unit for determining a biopsy position comprising the following units:

an interface embodied for the reception of an image data set of an examination volume, wherein the examination volume includes a tumor, a computing unit embodied for the segmentation of a tumor region in the image data set, furthermore embodied for the first determination of a texture distribution of the tumor region, wherein the texture distribution in each case assigns a texture parameter to image points in the tumor region, wherein each of the texture parameters is based on a spatial distribution of first intensity values of the image data set, furthermore embodied for the second determination of a biopsy position within the tumor region by applying an optimized position-determining algorithm to the texture distribution, wherein the optimized position-determining algorithm is based on training texture distributions and first training positions, wherein one of the first training positions is assigned to each of the training texture distributions.

Such a position-determining unit can in particular be embodied to carry out the above-described method according to embodiments of the invention for determining a biopsy position. The position-determining unit is embodied to carry out the methods and the embodiments thereof in that the interface and the computing unit are embodied to carry out the corresponding method steps.

An embodiment of the invention also relates to a computer-program product with a computer program and a computer-readable medium. An extensively software-based implementation has the advantage that it is also possible to retrofit position-determining units used to date in a simple way by a software update in order to work in the manner according to embodiments of the invention. In addition to the computer program, a computer-program product of this kind can optionally comprise additional parts, such as, for example, documentation and/or additional components and hardware components, such as, for example, hardware keys (dongles etc.) for using the software.

An embodiment of the invention also relates to a computer-program product comprising an optimized position-determining algorithm according to the method for optimizing a position-determining algorithm. This software-based implementation has the advantage that, following the incorporation of additional training data, the optimized position-determining algorithm can be forwarded to the position-determining units in a quick and simple manner. The invention furthermore relates to a computer-readable storage medium, which is embodied to be read by a position-determining unit comprising a computer-program product comprising an optimized position-determining algorithm according to embodiments of the method for optimizing a position-determining algorithm.

An embodiment of the invention can also relate to a training unit embodied for optimizing a position-determining algorithm comprising the following units:

a training interface embodied for the first reception of a first training image data set and a second training image data set of a training tumor region, furthermore embodied for the second reception of a position-determining algorithm, wherein the position-determining algorithm is based on a plurality of algorithm parameters, a training computing unit embodied for the first determination of a training texture distribution of the training tumor region, wherein the training texture distribution in each case assigns a training texture parameter to first training image points of the first training image data set, wherein each of the training texture parameters is based on a spatial distribution of first training intensity values of the first training image data set, furthermore embodied for the second determination of a first training position in the first training image data set based on a growth rate in the training tumor region, wherein the growth rate is based on the second training image data set, furthermore embodied for the third determination of a second training position by applying the position-determining algorithm to the training texture distribution, furthermore embodied for optimizing the position-determining algorithm by adjusting the algorithm parameters based on a comparison of the first training position with the second training position.

Such a training unit can in particular be embodied to carry out the above-described methods according to embodiments of the invention for optimizing a position-determining algorithm and the embodiments thereof. The training unit is embodied to carry out these methods and the embodiments thereof in that the training interface and the training computing unit are embodied to carry out the corresponding method steps.

An embodiment of the invention can also relate to a computer-program product with a computer program, which can be loaded directly into a training memory of a training unit, with program sections for carrying out all steps of embodiments of the methods when the program sections are executed by the training unit. An embodiment of the invention can also relate to a computer-readable storage medium on which program sections that can be read and executed by a training unit in order to carry out all the steps of the methods and the embodiments therefo, when the program sections are executed by the training unit. An extensively software-based implementation has the advantage that it is also possible to retrofit position-determining units used to date in a simple way by a software update in order to work in the manner according to at least one embodiment of the invention. In addition to the computer program, a computer-program product of this kind can optionally comprise additional parts, such as, for example, documentation and/or additional components and hardware components, such as, for example, hardware keys (dongles etc.) for using the software.

DETAILED DESCRIPTION OF THE EXAMPLE EMBODIMENTS

Figure 1:
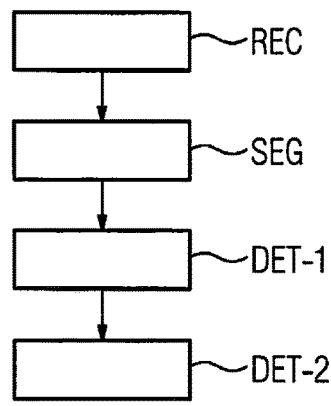
FIG. 1 shows a flow diagram of a method for determining a biopsy position.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the present invention is directed to a method where an image data set of an examination volume is received via an interface, wherein the examination volume includes a tumor. Furthermore, a tumor region is segmented in the image data set via a computing unit. Furthermore, a texture distribution of the tumor region is determined via the computing unit, wherein the texture distribution in each case assigns a texture parameter to image points in the tumor region, wherein each of the texture parameters is based on a spatial distribution of first intensity values of the image data set. Furthermore, a biopsy position within the tumor region is determined by applying an optimized position-determining algorithm to the texture distribution via the computing unit, wherein the optimized position-determining algorithm is based on training texture distributions and first training positions, wherein one of the first training positions is assigned to each of the training texture distributions.

Here, a tumor region can in particular be a coherent and/or a non-coherent region in the image data set. A texture distribution can in particular assign a texture parameter to only one selection of image points in the tumor region or to all image points in the tumor region. A position-determining algorithm can in particular be implemented via an artificial intelligence system.

The inventors have recognized that activity in the regions of a tumor can be determined particularly effectively and efficiently from the texture of the intensity distribution in the image data set. The calculation of a texture distribution of texture parameters furthermore enables the texture, and hence the activity of the tumor, to be acquired and determined in a locally resolved manner. The use of an optimized position-determining algorithm, in particular an artificial intelligence system, enables all relevant influencing variables for the determination of the biopsy position to be taken into account, including those for which a user is unable to estimate any relationship between the activity of the tumor and the influencing variable.

According to a further embodiment of the invention, each of the texture parameters is based on the spatial distribution of the first intensity values in a surrounding area around the assigned image point. In particular, each of the texture parameters is not based on the first intensity values outside the surrounding area around the assigned image point. A surrounding area can in particular also be identical to the tumor region. The inventors have recognized that calculation only in a local surrounding area around an image data point is quicker than calculation in the entire tumor region and that the use of such surrounding areas can improve the spatial resolution of the texture distribution.

According to a further embodiment of the invention, each of the texture parameters is based on the spatial distribution of the first intensity values in the intersection of the tumor region and a surrounding area around the assigned image point. In particular, each of the texture parameters is not based on the first intensity values outside the intersection of the tumor region and a surrounding area around the assigned image point. The inventors have recognized that, as a result of this restriction, regions of the image data set outside the tumor region have no influence on the texture distribution and hence on the biopsy position and consequently the determination of the biopsy position will be more precise and less susceptible to error.

According to a further embodiment of the invention, each of the surrounding areas around one of the assigned image points has the same geometric shape and the same orientation, furthermore each of the surrounding areas around of the assigned image points has the same position relative to the one of the assigned image points. The inventors have recognized that the use of uniform surrounding areas of this kind enables each of the texture parameters to be calculated particularly quickly and also parallelized, furthermore this renders the texture parameters easier to compare with one another, thus resulting in a determination of the biopsy position that is more precise and less susceptible to error.

According to a further possible embodiment of the invention, each of the surrounding areas around of the assigned image points has a circular or spherical shape, furthermore, with each of the surrounding areas around of the assigned image points, the one of the assigned image points lies in the center of the respective surrounding area. According to a further possible embodiment of the invention, each of the surrounding areas around of the assigned image points has a square or cube shape, furthermore, with each of the surrounding areas around of the assigned image points, the one of the assigned image points lies in the center of the respective surrounding area. The inventors have recognized that, as a result of the selection of a symmetrical surrounding area of this kind, each of the texture parameters does not depend, or only depends to a small degree, on the orientation of the image data set. Since the orientation of the image data set does not contain any information on the activity of the tumor, the selection of such surrounding areas enables the determination of the biopsy position to be more precise and less susceptible to error.

According to a further embodiment of the invention, each of the texture parameters is based at least on a histogram, a graytone matrix, a convolution with a convolution window, an autocorrelation and/or a transform in each case of the first intensity values of the image data set. In particular, each of the texture parameters can be based at least on a histogram, a graytone matrix, a convolution with a convolution window, an autocorrelation and/or a transform in each case of the first intensity values of the image data set in a surrounding area around the assigned image point in each case.

In a particular embodiment, each of the texture parameters can be based at least on a histogram, a graytone matrix, a run-length matrix, a convolution with a convolution window, an autocorrelation and/or a transform in each case of the first intensity values of the image data set in the intersection of the tumor region and a surrounding area around the image point assigned in each case. A transform can in particular be a Fourier transform or a wavelet transform. The inventors have recognized that the variables listed enable the spatial distribution of the first intensity values, and hence the texture of the first intensity values, to be characterized particularly effectively and therefore the biopsy position can be determined in a particularly quick and precise manner.

According to a further embodiment of the invention, each of the texture parameters comprises at least one scaling-invariant variable, wherein the scaling-invariant variable is based on the first intensity values of the image data set in the tumor region, and wherein, on statistical average, the scaling-invariant variable is independent of the spatial resolution of the image data set. A scaling-invariant variable is in particular a moment or a central moment of the first intensity values of the image data set in the tumor region. The inventors have recognized that, as a result of the use of a scaling-invariant variable, the texture parameter is not dependent on the spatial resolution of the image data set and the method is, therefore, simple to apply to image data sets with different resolutions.

According to a further embodiment of the invention, each of the texture parameters is a measure for the shape and/or a measure for the structure of the tumor. A measure for the shape in particular quantifies the geometry of the tumor and/or the tumor region. A measure for the structure in particular quantifies local deviations in the first intensity values. The inventors have recognized that such texture parameters are particularly suitable for quantifying the activity in the tumor region and therefore result in a particularly precise determination of the biopsy position.

According to a further embodiment of the invention, each of the texture parameters is furthermore based on a spatial distribution of second intensity values of the image data set. The inventors have recognized that this enables addition information on the tumor region to be acquired which results in a determination of the biopsy position that is more precise and less susceptible to error.

According to a further embodiment of the invention, the first and the second intensity values are in each case computed tomography Hounsfield intensity values, wherein the first intensity values were acquired with a first X-ray energy, wherein the second intensity values were acquired with a second X-ray energy and wherein the first X-ray energy is greater than the second X-ray energy. The inventors have recognized that the use of intensities with two different X-ray energies enables different tissue types to be differentiated particularly effectively by way of the distribution of the first and the second intensity values and that the use of a texture parameter based thereupon renders the determination of a biopsy position more precise and less susceptible to error.

According to a further embodiment of the invention, the first intensity values are computed tomography Hounsfield intensity values, furthermore, the wide intensity values are positron-emission-tomography intensity values, wherein positron-emission-tomography intensity values are a measure for a number of emitted positrons. The inventors have recognized that positron-emission-tomography intensity values describe the metabolic activity in a region particularly effectively and that, simultaneously, computed tomography Hounsfield intensity values have particularly good spatial resolution. Hence, a combination of these two intensity values results in improved recognition of tumor activity and in a determination of the biopsy position that is more precise and less susceptible to error.

According to a further possible embodiment of the invention, each of the first training positions is based on a growth rate in a training tumor region. In particular, the optimized position-determining algorithm is based on training texture distributions and first training positions, wherein each of the training texture distributions is based on a first training image data set and wherein the growth rate is based on a second training image data set.

According to a further possible embodiment of the invention, the second training image data set is a positron-emission training image data set and the growth rate in a second training image data point of the second training image data set is directly proportional to the number of detected electron-positron pairs in the second training image data point.

According to a further possible embodiment of the invention, the acquisition time point of the first training image data set is chronologically later than the acquisition time point of the second training image data set and the growth rate is determined based on a comparison of the first training image data set and the second training image data set.

According to a further possible embodiment of the invention, the optimized position-determining algorithm is an artificial neural network or a Bayesian network, wherein in particular the edge weights of the artificial neural network or the Bayesian network are optimized.

The method according to an embodiment of the invention for optimizing a position-determining algorithm is based on the principle that a first training image data set and a second training image data set of a training tumor region is received via a training interface. Furthermore, a training computing unit determines a training texture distribution of the training tumor region, wherein the training texture distribution in each case assigns a training texture parameter to first training image points of the first training image data set and wherein each of the training texture parameters is based on a spatial distribution of first training intensity values of the first training image data set.

Furthermore, based on a growth rate in the training tumor region, a first training position is determined via the training computing unit, wherein the growth rate is based on the second training image data set. Furthermore, the training interface receives a position-determining algorithm, wherein the position-determining algorithm is based on a plurality of algorithm parameters. Furthermore, the training computing unit determines a second training position by applying the position-determining algorithm to the training texture distribution. Furthermore, the training computing unit optimizes a position-determining algorithm by adjusting the algorithm parameters based on a comparison of the first training position with the second training position. Herein, a position-determining algorithm can in particular be an artificial intelligence system.

The inventors have recognized that the activity in the region of a tumor can be determined particularly effectively and efficiently from the texture of the first training intensity distribution in the training image data set. The calculation of a training texture distribution of training texture parameters furthermore enables the activity of the tumor to be acquired and determined in a locally resolved manner. The determination of the second training position based on a growth rate enables the activity in the training tumor region to be determined in a particularly simple and precise manner. The comparison of the first and the second training position enables the algorithm parameters of the position-determining algorithm to be adjusted in a particularly simple and quick manner.

According to a further embodiment of the invention, the second training image data set is a positron-emission training image data set, wherein the growth rate in a second training image data point of the second training image data set is directly proportional to the number of detected electron-positron pairs in the second training image data point. The inventors have recognized that a positron-emission training image data set can be used to determine metabolic activity in the tumor region that has a positive correlation to the growth rate of the tumor. Therefore, the training position can be determined in a particularly simple and precise manner based on the growth rate.

According to a further embodiment of the invention, the acquisition time point of the first training image data set is chronologically later than the acquisition time point of the second training image data set and wherein the growth rate is determined based on a comparison of the first training image data set and the second training image data set. The inventors have recognized that, on the removal of a biopsy, in many cases chronologically disparate items of image data are already present. A comparison of this image data enables the growth rate to be determined without acquiring a separate training image data set for this purpose. Hence, this variant of the method can be carried out in a particularly cost-effective manner.

According to a further embodiment of the invention, the position-determining algorithm is an artificial neural network or a Bayesian network, wherein the algorithm parameters are the edge weights of the artificial neural network or the Bayesian network. The inventors have recognized that the use of an artificial neural network or a Bayesian network enables the training to be carried out in a particularly efficient and quick manner.

According to a further possible embodiment of the invention, each of the training texture parameters is based on the spatial distribution of the first training intensity values in a surrounding area around the assigned training image point.

According to a further possible embodiment of the invention, each of the surrounding areas around of the assigned training image points has the same geometric shape and the same orientation, wherein, with each of the surrounding areas, one of the assigned training image points has the same position relative to the one of the assigned training image points.

According to a further possible embodiment of the invention, each of the training texture parameters is based at least on a histogram, a graytone matrix, a run-length matrix, a convolution with a convolution window, an autocorrelation and/or a transform in each case of the first intensity values of the first training image data set.

According to a further possible embodiment of the invention, each of the training texture parameters comprises at least one scaling-invariant variable, wherein the scaling-invariant variable is based on the first training intensity values of the first training image data set in the training tumor region and wherein, on statistical average, the scaling-invariant variable is independent of the spatial resolution of the first training image data set.

According to a further possible embodiment of the invention, each of the training texture parameters is a measure for the shape and/or a measure for the structure of the training tumor region.

According to a further possible embodiment of the invention, each of the training texture parameters is furthermore based on a spatial distribution of second training intensity values of the first training image data set.

According to a further possible embodiment of the invention, the first and the second training intensity values are in each case computed tomography Hounsfield intensity values, wherein the first training intensity values were acquired with a first X-ray energy, wherein the second training intensity values were acquired with a second X-ray energy and wherein the first X-ray energy is greater than the second X-ray energy.

According to a further possible embodiment of the invention, the first training intensity values are computed tomography Hounsfield intensity values and the second training intensity values are positron-emission-tomography intensity values, wherein positron-emission-tomography intensity values are a measure for a number of emitted positrons.

An embodiment of the invention furthermore relates to a position-determining unit for determining a biopsy position comprising the following units:

an interface embodied for the reception of an image data set of an examination volume, wherein the examination volume includes a tumor, a computing unit embodied for the segmentation of a tumor region in the image data set, furthermore embodied for the first determination of a texture distribution of the tumor region, wherein the texture distribution in each case assigns a texture parameter to image points in the tumor region, wherein each of the texture parameters is based on a spatial distribution of first intensity values of the image data set, furthermore embodied for the second determination of a biopsy position within the tumor region by applying an optimized position-determining algorithm to the texture distribution, wherein the optimized position-determining algorithm is based on training texture distributions and first training positions, wherein one of the first training positions is assigned to each of the training texture distributions.

Such a position-determining unit can in particular be embodied to carry out the above-described method according to embodiments of the invention for determining a biopsy position. The position-determining unit is embodied to carry out the methods and the embodiments thereof in that the interface and the computing unit are embodied to carry out the corresponding method steps.

An embodiment of the invention also relates to a computer-program product with a computer program and a computer-readable medium. An extensively software-based implementation has the advantage that it is also possible to retrofit position-determining units used to date in a simple way by a software update in order to work in the manner according to embodiments of the invention. In addition to the computer program, a computer-program product of this kind can optionally comprise additional parts, such as, for example, documentation and/or additional components and hardware components, such as, for example, hardware keys (dongles etc.) for using the software.

An embodiment of the invention also relates to a computer-program product comprising an optimized position-determining algorithm according to the method for optimizing a position-determining algorithm. This software-based implementation has the advantage that, following the incorporation of additional training data, the optimized position-determining algorithm can be forwarded to the position-determining units in a quick and simple manner. The invention furthermore relates to a computer-readable storage medium, which is embodied to be read by a position-determining unit comprising a computer-program product comprising an optimized position-determining algorithm according to embodiments of the method for optimizing a position-determining algorithm.

An embodiment of the invention can also relate to a training unit embodied for optimizing a position-determining algorithm comprising the following units:

a training interface embodied for the first reception of a first training image data set and a second training image data set of a training tumor region, furthermore embodied for the second reception of a position-determining algorithm, wherein the position-determining algorithm is based on a plurality of algorithm parameters, a training computing unit embodied for the first determination of a training texture distribution of the training tumor region, wherein the training texture distribution in each case assigns a training texture parameter to first training image points of the first training image data set, wherein each of the training texture parameters is based on a spatial distribution of first training intensity values of the first training image data set, furthermore embodied for the second determination of a first training position in the first training image data set based on a growth rate in the training tumor region, wherein the growth rate is based on the second training image data set, furthermore embodied for the third determination of a second training position by applying the position-determining algorithm to the training texture distribution, furthermore embodied for optimizing the position-determining algorithm by adjusting the algorithm parameters based on a comparison of the first training position with the second training position.

Such a training unit can in particular be embodied to carry out the above-described methods according to embodiments of the invention for optimizing a position-determining algorithm and the embodiments thereof. The training unit is embodied to carry out these methods and the embodiments thereof in that the training interface and the training computing unit are embodied to carry out the corresponding method steps.

An embodiment of the invention can also relate to a computer-program product with a computer program, which can be loaded directly into a training memory of a training unit, with program sections for carrying out all steps of embodiments of the methods when the program sections are executed by the training unit. An embodiment of the invention can also relate to a computer-readable storage medium on which program sections that can be read and executed by a training unit in order to carry out all the steps of the methods and the embodiments therefo, when the program sections are executed by the training unit. An extensively software-based implementation has the advantage that it is also possible to retrofit position-determining units used to date in a simple way by a software update in order to work in the manner according to at least one embodiment of the invention. In addition to the computer program, a computer-program product of this kind can optionally comprise additional parts, such as, for example, documentation and/or additional components and hardware components, such as, for example, hardware keys (dongles etc.) for using the software.

An image data set is an at least two-dimensional image data set and comprises one or more at least two-dimensional representations of an examination volume. Each of the representations can comprise a plurality of pixels or voxels to which an intensity value is assigned. The intensity value of one of the pixels or voxels can quantify the strength of a physical, biological and/or chemical property in a part of the examination volumes, wherein the part of the examination volumes corresponds to the original image of the one of the pixels or voxels.

A texture is in particular a measure for the spatial variability and/or the spatial non-uniformity of intensity values. A texture can in particular relate to the smoothness, the coarseness (an English technical term; a German translation is Grobkörnigkeit) and regularity of the intensity values. A texture parameter is a variable that quantifies a texture, in particular a variable that is dependent on intensity values, in particular the spatial distribution of intensity values.

A histogram of intensity values of the image data set and/or in the tumor region is in particular the frequency distribution of the intensity values. Such a histogram is in particular an assignment of individual intensity values to the absolute or relative frequency of their occurrence in the intensity values. Herein, it is possible in each case for one more intensity values to be divided into classes and the absolute or relative frequency of classes to be considered. From a histogram of intensity values of the image data set and/or in the tumor region, it is in particular possible to derive variables of the intensity values that are not dependent on the spatial coordinates of the intensity values.

In the case of a two-dimensional image data set, a graytone matrix G is in particular a symmetrical N×N matrix, which is dependent on intensity values $I(x,y)$ divided into N classes $K_n$ (n=1 ... N) and on a horizontal distance $\Delta x$ and a vertical distance $\Delta y$. Herein, the entry $G_{mn}$ in the m-th row and the n-th column counts the number of pairs comprising a first pixel and a second pixel, wherein the first pixel and the second pixel have the prespecified horizontal and vertical distance and wherein the first pixel has an intensity value from the m-th class of the intensity values and the second pixel has an intensity value from n-th class of the intensity values:

$$G_{mn}(I,\Delta x,\Delta y)=|\{(x,y)|I(x,y)\epsilon K_m, I(x+\Delta x,y+\Delta y)\epsilon K_n\}|$$

A graytone matrix can also be normalized. In the case of spatially homogeneous intensity values, the values of the graytone matrix close to the main diagonals tend to be higher than those remote from the main diagonals; in the case of spatially inhomogeneous intensity values, the values of the graytone matrix close to the main diagonals tend to be smaller than those remote from the main diagonals. In the case of a three-dimensional or a four-dimensional image data set, the graytone matrix can be defined similarly in that distances in the additional dimensions are taken into account:

$$G_{mn}(I,\Delta \vec{x})=|\{\vec{x}|I(\vec{x})\epsilon K_m, I(\vec{x}+\Delta \vec{x})\epsilon K_n\}|$$

In the case of a two-dimensional image data set, a run-length matrix L with respect to a direction of evaluation is a N×R matrix, which is dependent on the intensity values I(x,y) divided into N classes $K_n$ (n=1 . . . N). The number R designates the maximum extension of the two-dimensional image data set with respect to the direction of evaluation. In particular, directions of evaluation are considered that are a multiple of 45°. If the direction of evaluation is 0° or 180° (horizontal), R corresponds to the horizontal extension of the image data set in pixels. If the direction of evaluation is 90° or 270° (vertical), R corresponds to the vertical extension of the image data set in pixels. If the direction of evaluation is an uneven multiple of 45°, R corresponds to the minimum value of horizontal and vertical extension of the image data set in pixels. The entry $L_{mr}$ in the run-length matrix is the number of r-tuples in sequential pixels with graytones exclusively from the m-th class, wherein the sequence of pixels is defined by the direction of evaluation.

A convolution (I*F) of the intensity values I(x, y) of the image data set and/or in the tumor region with a convolution window F(x, y) can in particular be calculated as:

$$(I*F)(x,y) = \sum_{x',y'} I(x',y')F(x-x',y-y')$$

Herein, the convolution core in particular only has values different from 0 in a small surrounding area around the origin (x=y=0). A convolution can also be determined in a similar way for more than two-dimensional image data sets. A convolution can in particular be calculated in a particularly simple manner as an inverse Fourier transform of the mode-by-mode product of the Fourier transforms of the intensity values and the Fourier transforms of the convolution core. Herein, it is in particular possible to use a fast Fourier transform (an English technical term, "FFT" for short; a German translation is "schnelle Fourier Transformation").

Autocorrelation A(Δx, Δy) describes the correlation of pixels of the intensity values in the image data set and/or in the tumor region, wherein the pixels have a prespecified distance:

$$A(\Delta x, \Delta y) = \frac{1}{\text{Var}(I)} \sum_{x,y} I(x,y)I(x+\Delta x, y+\Delta y)$$

Herein, Var(I) designates the variance of the intensity values. Autocorrelation can be used to assess the spatial homogeneous or inhomogeneous structure of the intensity values.

In the case of a transform of intensity values of the image data set and/or in the tumor region, the coefficients of the representation are calculated in another base or with other basic functions. A transform can in particular be a Fourier transform of the intensity values and/or a wavelet transform of the intensity values. A Fourier transform is in particular a discrete Fourier transform. A wavelet transform is in particular a discrete wavelet transform. In the case of a Fourier transform, in particular trigonometric functions, such as sine and cosine, are used as basic functions. In the case of a wavelet transform, in particular wavelets are used as the basic function.

FIG. 1 shows a flow diagram of an example embodiment of a method for determining a biopsy position.

The first step of the example embodiment is the reception REC of an image data set of an examination volume via an interface 301 of the position-determining unit 300, wherein the examination volume includes a tumor. In this example embodiment, the image data set is a spatially two-dimensional image data set. Alternatively, the image data set can also be a three-dimensional image data set, in particular a spatially three-dimensional image data set, or a four-dimensional image data set. In the example embodiment depicted, the examination volume is located inside a patient. In this example embodiment, the image data set comprises first computed-tomography intensity values, wherein Hounsfield units are assigned to pixels of the image data set. However, alternatively, the image data set can also comprise intensity values from other imaging medical devices, for example positron-emission spectroscopy intensity values. Furthermore, the image data set can also comprise second intensity values, wherein the second intensity values are, for example, computed-tomography intensity values with a different X-ray energy than the first computed-tomography intensity values or wherein the second intensity values were acquired by a different imaging medical device or by way of a different imaging medical method than the first intensity values or wherein the second intensity values were acquired at a different time point than the first intensity values.

A computed tomograph or computed-tomography is generally referred to a "CT" for short. CT intensity values with two different X-ray energies can be acquired with dual-source CT (an English technical term; a German translation is "Zwei-Quellen-CT"), spectral CT or single-source CT, wherein in the case of single-source CT, two images are acquired with different X-ray energies in direct chronological proximity.

In the example embodiment, it is alternatively also possible for more than two CT intensity values to be used with different X-ray energies in each case. To acquire more than two CT intensity values of this kind, it is in particular possible to use photon-counting X-ray detectors in the CT.

The first CT intensity values with a first X-ray energy can be ascertained by direct measurement in a CT, wherein the first X-ray energy is set in the case of an X-ray emitter or filtered in the case of an X-ray detector. Alternatively, the first CT intensity values with a first X-ray energy can also be ascertained from other CT intensity values with other X-ray energies (an English technical term for this is "monoenergetic CT").

First and/or second intensity values can also be obtained from imaging examinations with a contrast medium in the examination volume. Computed-tomography using a contrast medium is also referred to as "perfusion CT". Herein, the first and/or second intensity values can be acquired at different times following the administration of the contrast medium. This in particular entails acquisition in the arterial phase (an English technical term; a German translation is "arterielle Phase"), in the venous phase (an English technical term; a German translation is "venöse Phase") or in a delayed phase (an English technical term; a German translation is "verspätete Phase"), wherein the different phases designate different times between the administration of the contrast medium and the imaging examination.

The next step in the example embodiment is the segmentation SEG of the tumor region 501 in the image data set via a computing unit 302 of the position-determining unit 300. In the example embodiment depicted, during the acquisition of the first intensity values, the examination volume included an X-ray contrast medium, which in particular accumulates in a tumor. Therefore, here, the segmentation can be performed by way of threshold segmentation. However, it is alternatively also possible to use other segmentation methods, for example edge-oriented methods. Furthermore, it is alternatively also possible to perform threshold segmentation without the X-ray contrast medium in the examination volume.

The next step of the example embodiment depicted is the first determination DET-1 of a texture distribution of the tumor region 501 via the computing unit 302 of the position-determining unit 300, wherein the texture distribution in each case assigns a texture parameter to image points 502.1, 502.2 in the tumor region 501 and wherein each of the texture parameters is based on a spatial distribution of first intensity values of the image data set.

In this example embodiment, the texture distribution assigns a texture parameter to each of the image points 502.1, 502.2 of the tumor region 501. Therefore, the texture distribution can also be understood to be a texture image data set with the same spatial resolution as the image data set. Alternatively, the texture distribution can also assign a texture parameter to only a genuine subset of the image points 502.1, 502.2 of the tumor region 501.

In the example embodiment depicted, each of the texture parameters of an image point 502.1, 502.2 is in each case based on the first intensity values in a surrounding area 503.1, 503.2 around the image point 502.1, 502.2. In the example embodiment, the surrounding area 503.1, 503.2 around an image point 502.1, 502.2 with the coordinate (x, y) is defined by all image points with the coordinates (x+$\Delta$x, y+$\Delta$y), wherein |$\Delta$x|+|$\Delta$y| is smaller than or equal to a given threshold value, in this example embodiment 3. Alternatively, the surrounding area 503.1, 503.2 can also have a square shape, i.e. include all image points with coordinates (x+$\Delta$x, y+$\Delta$y), wherein |$\Delta$x| is smaller than or equal to a given threshold value and simultaneously |$\Delta$y| is smaller than or equal to the given threshold value, wherein, here, the threshold value is half the side length of the surrounding area 503.1, 503.2. Alternatively, the surrounding area 503.1, 503.2 can also have a circular shape, i.e. include all image points with coordinates (x+$\Delta$x, y+$\Delta$y), wherein the second root of the sum of the squares ($\Delta$x)$^2$ and ($\Delta$y)$^2$ is smaller than or equal to a given threshold value, wherein, here, the threshold value is the radius of the surrounding area 503.1, 503.2.

In the example embodiment depicted, all first intensity values in the respective surrounding area 503.1, 503.2 are included in the calculation of the texture parameter, i.e. including intensity values outside the tumor region 501. Alternatively, it is also possible for only intensity values in the section 504.1, 504.2 of the respective surrounding area 503.1, 503.2 with the tumor region 501 to be included in the calculation of the texture parameter, i.e. in particular no intensity values 505 outside the tumor region 501.

In the example embodiment depicted, the variance of the first intensity values in the surrounding area 503.1, 503.2 around the image point 502.1, 502.2 is used as the texture parameter of an image point 502.1, 502.2. However, it is alternatively also possible to use other texture parameters or combinations of other texture parameters. Possible texture parameters are:

The next method step of the example embodiment depicted is the second determination (DET-2) of a biopsy position within the tumor region 501 by applying an optimized position-determining algorithm to the texture distribution via the computing unit 302 of the position-determining unit 300, wherein the optimized position-determining algorithm is based on training texture distributions 423.1, 423.2 and first training positions 424.1, 424.2, wherein one of the first training positions 424.1, 424.2 is assigned to each of the training texture distributions 423.1, 423.2.

In the example embodiment depicted, each of the first training positions 424.1, 424.2 is based on a growth rate in a training tumor region. In particular, the optimized position-determining algorithm is based on training texture distributions 423.1, 423.2 and first training positions 424.1, 424.2, wherein each of the training texture distributions is based on a first training image data set 421.1, 421.2 and wherein the growth rate is based on a second training image data set 422.1, 422.2. In the example embodiment depicted, the second training image data set 422.1, 422.2 is a positron-emission-tomography image data set. Alternatively, it is also possible that the first training image data set 421.1, 421.2 and the second training image data set 422.1, 422.2 were acquired at two different time points and the growth rate is based on a comparison of the first training image data set 421.1, 421.2 and the second training image data set 422.1, 422.2.

Alternatively, it is also possible that the training texture distribution 423.1, 423.2 was determined synthetically by way of a model and the first training position 424.1, 424.2 can be determined on the basis of the model used. Alternatively, it is furthermore possible that the training texture distribution 423.1, 423.2 is based on a first training image data set 421.1, 421.2 of a real examination volume, which has been modified on the basis of a model, wherein the first training position 424.1, 424.2 can be determined on the basis of the model used (an English technical term is "lesion insertion"). Furthermore, it is also possible that the training texture distribution 423.1, 423.2 is based on a first training image data set 421.1, 421.2 of a training phantom, wherein the first training position 424.1, 424.2 can be determined on the basis of the phantom used.

Herein, the optimized position-determining algorithm is defined by an artificial neural network the algorithm parameters of which are defined by the edge weights. Alternatively, it is also conceivable that the optimized position-determining algorithm is a Bayesian network or another artificial intelligence system. The optimized position-determining algorithm was optimized with the method depicted in FIG. 2.

The artificial neural network used here comprises a plurality of slices of nodes, wherein in each case nodes from adjacent slices are connected to edges. The first slice of the artificial neural network is also called the input slice. In this example embodiment, the input slice comprises M·N·D nodes, wherein M is greater than the maximum horizontal extension of the tumor region 501 measured in a number of image points, wherein N is greater than the maximum vertical extension of the tumor region 501 measured in a number of image points and wherein D is a dimensionality of the texture parameter. The dimensionality of the texture parameter is the number of real numbers required to quantify the texture parameter completely. In this example embodiment, the texture parameter corresponds to the variance of first intensity values, these can be depicted with a real number, i.e. D=1. If, alternatively, the texture parameter comprises a plurality of real numbers, D is the quantity of these numbers.

In order to assign values to the nodes of the input slice, in the example embodiment depicted, the variances assigned to the image points 502.1, 502.2 of the tumor region 501 are embedded in an image with M×N pixels. In the example embodiment depicted, the variance of the image pixel with the coordinates (x,y) is assigned to the (y·M+x)-th nodes of the input slice; if there is no variance at this image pixel (for example because this image pixel lies outside the tumor region 501), the value −1 is assigned to this node.

Alternatively, if the dimensionality of the tumor parameter is greater than one, the first components of the texture parameters assigned to the image points 502.1, 502.2 of the tumor region 501 are embedded in a first image with M×N pixels and the (d+1)-th components of the texture parameters assigned to the image points 502.1, 502.2 of the tumor region 501 are embedded in a (d+1)-th image with M×N pixels, wherein d is a whole number between 0 and (D−1). Then the value of the image pixel with the coordinates (x,y) in the (d+1)-th image is assigned to (d·M·N+y·M+x)-th node of the input slice.

In the example embodiment depicted, the output slice of the artificial neural network comprises M·N output nodes. The propagation of the input values of the input nodes by the network provided with edge weights causes a biopsy weight of the image pixel with the coordinates (x,y) in one of the images to be assigned to (y·M+x)-th node of the output slice. The image pixel assigned to the output node with the maximum biopsy weight then defines the biopsy position.

In the example embodiment depicted, the steps of the method are performed in the sequence depicted in FIG. 1.

Figure 2:
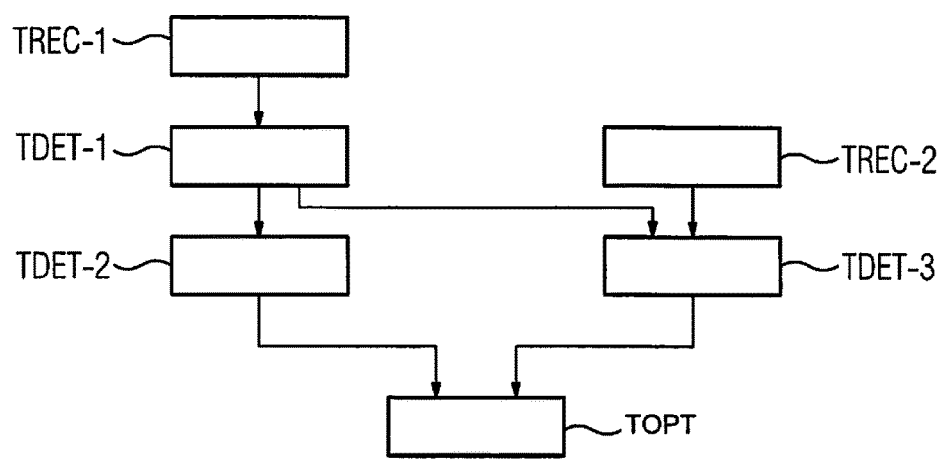
FIG. 2 shows a flow diagram of a method for optimizing a position-determining algorithm.

FIG. 2 shows a flow diagram of an example embodiment of the method for optimizing a position-determining algorithm.

The first step of the example embodiment depicted is the first reception TREC-1 of a first training image data set 421.1, 421.2 and a second training image data set 422.1, 422.2 of a training tumor region via a training interface 401 of the training unit 400. Herein, the first training image data set 421.1, 421.2 and the second training image data set 422.1, 422.2 are in each case an image data set of the same training tumor region. In this example embodiment, the first training image data set 421.1, 421.2 is a computed-tomography-image data set and the second training image data set 422.1, 422.2 is a positron-emission spectroscopy-image data set, which was acquired in direct chronological proximity, in particular with a time difference of less than one minute, for example via a combined imaging medical device.

The next step of the example embodiment depicted is the first determination TDET-1 of a training texture distribution 423.1, 423.2 of the training tumor region via a training computing unit 402, wherein the training texture distribution 423.1, 423.2 in each case assigns a training texture parameter to first training image points of the first training image data set 421.1, 421.2 and wherein each of the training texture parameters is based on a spatial distribution of first training intensity values of the first training image data set 421.1, 421.2.

The next step of the example embodiment depicted is the second determination TDET-2 of a first training position 424.1, 424.2 in the first training image data set 421.1, 421.2 based on a growth rate in the training tumor region via the training computing unit 402, wherein the growth rate is based on the second training image data set 422.1, 422.2. Here, the first training position 424.1, 424.2 used is the position in the PET-image data set with the highest PET activity, since the PET activity is correlated positively with the metabolism and hence the growth rate in the tumor region 501.

The next step of the example embodiment depicted is the second reception TREC-2 of a position-determining algorithm via the training interface 401 of the training unit 400, wherein the position-determining algorithm is based on a plurality of algorithm parameters. In the example embodiment depicted, the position-determining algorithm is defined by an artificial neural network; the algorithm parameters are defined by the edge weights of the artificial neural network. The artificial neural network has the same geometry and the same properties as the artificial neural network of the optimized position-determining algorithm described in FIG. 1.

The next step of the example embodiment depicted is the third determination TDET-3 of second training position by applying the position-determining algorithm to the training texture distribution 423.1, 423.2 via the training computing unit 402. The application is performed in the same way as the application of the optimized position-determining algorithm described for FIG. 1.

The next step of the example embodiment depicted is the optimization TOPT of the position-determining algorithm by adjusting the algorithm parameters based on a comparison of the first training position 424.1, 424.2 with the second training position via the training computing unit 402. In this example embodiment, the square distance of the first training position 424.1, 424.2 and the second training position is used as a measure for the deviation. This deviation is used by way of backpropagation (an English technical term; a German translation is "Rückpropagation") to adjust the edge weights of the artificial neural network. Alternatively, it is also possible to use other variables as a measure of the deviation. Alternatively, it is additionally also possible to use other algorithms to optimize the edge weights.

Figure 3:
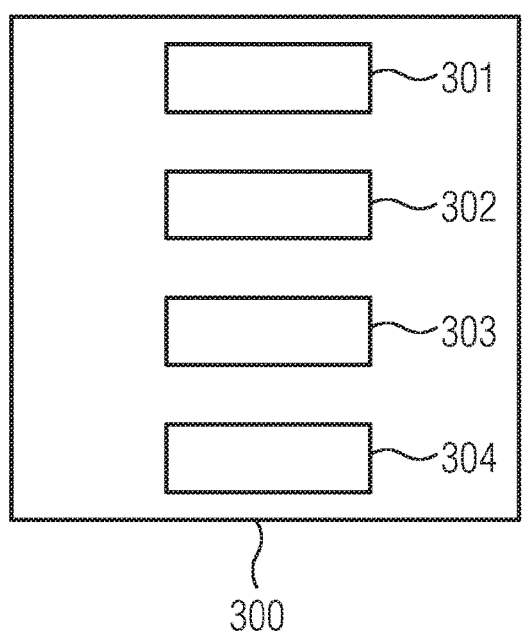
FIG. 3 shows a position-determining unit.
Figure 4:
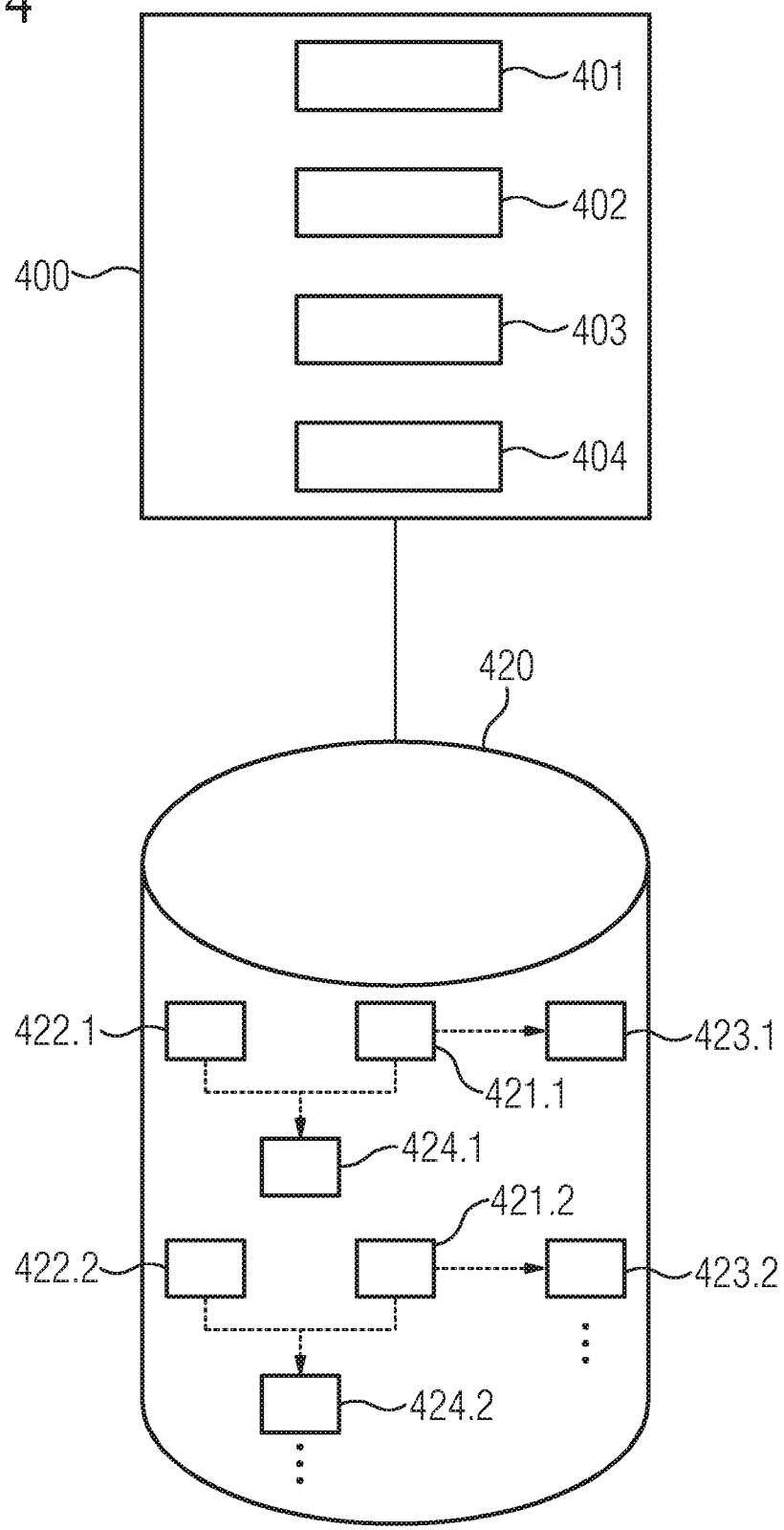
FIG. 4 shows a training unit.

FIG. 3 shows a position-determining unit 300 for determining a biopsy position, FIG. 4 shows a training unit 400 for optimizing a position-determining algorithm. The position-determining unit 300 shown in FIG. 3 is designed to carry out a method according to the invention for determining a biopsy position. The training unit 400 shown in FIG. 4 is designed to carry out a method according to the invention for optimizing a position-determining algorithm.

The position-determining unit 300 comprises an interface 301, a computing unit 302, a storage unit 303 and an input and output unit 304. The training unit 400 comprises a training interface 401, a training computing unit 402, a training storage unit 403 and a training input and training output unit 404. The position-determining unit 300 and/or the training unit 400 can in particular be a computer, a microcontroller or an integrated circuit. Alternatively, the position-determining unit 300 and/or the training unit 400 can be a real or virtual group of computers (an English technical term for a real group is "cluster", an English technical term for a virtual group is "cloud"). An interface 301 and a training interface 401 can in each case be a hardware or software interface (for example, PCI bus, USB or Firewire). A computing unit 302 and a training computing unit 402 can in each case comprise hardware elements or software elements, for example a microprocessor or a socalled FPGA (an English abbreviation for "field programmable gate array"). A storage unit 303 and a training storage unit 403 can in each case be implemented as non-permanent working memories (random access memory, RAM for short) or as a permanent mass memories (hard disk, USB stick, SD card, solid state disk). An input and output unit 304 and a training input and training output unit 404 in each case comprises at least one input unit and/or at least one output unit. An input unit can in particular be implemented as a keyboard, a mouse or a touch-sensitive screen, an output unit can in particular be implemented as a screen or a printer. An input and output unit 304 and a training input and training output unit 404 can in particular also be implemented by a touch-sensitive screen (an English technical term is "touchpad") or by a portable interactive device, for example a tablet computer.

In the example embodiment depicted, the training unit 400 is connected to a training database 420. The training database comprises first training image data sets 421.1, 421.2, second training image data sets 422.1, 422.2, training texture distributions 423.1, 423.2 and first training positions 424.1, 424.2. Alternatively, it is also possible for the database only to comprise training texture distributions 423.1, 423.2 and first training positions 424.1, 424.2. Alternatively, it is also possible for the database only to comprise first training image data sets 421.1, 421.2 and second training image data sets 422.1, 422.2. In the example embodiment depicted, the training database 420 is embodied as separate from the training unit 400, for example via a separate database server. However, the database can also be stored in the training storage unit 403 of the training unit. If, as depicted in the example embodiment, a training database 420 is connected to the training unit 400, the first reception can be performed by fetching a first training image data set 421.1, 421.2 and a second training image data set 422.1, 422.2 from the database.

Both the position-determining unit 300 and the training unit 400 can be embodied as a real or virtual group of computer and/or computing units. Herein, it is in particular possible for the storage unit 303 to be separate from the computing unit 302 and/or the training storage unit 403 to be separate from the training computing unit 402. In particular, it is also possible for the storage unit 303 and the computing unit 302 to be divided between several computers and/or computing units embodied to communicate with one another. In particular, it is also possible for the training storage unit 403 and the training computing unit 402 to be divided between several computers and/or computing units embodied to communicate with one another.

Figure 5:
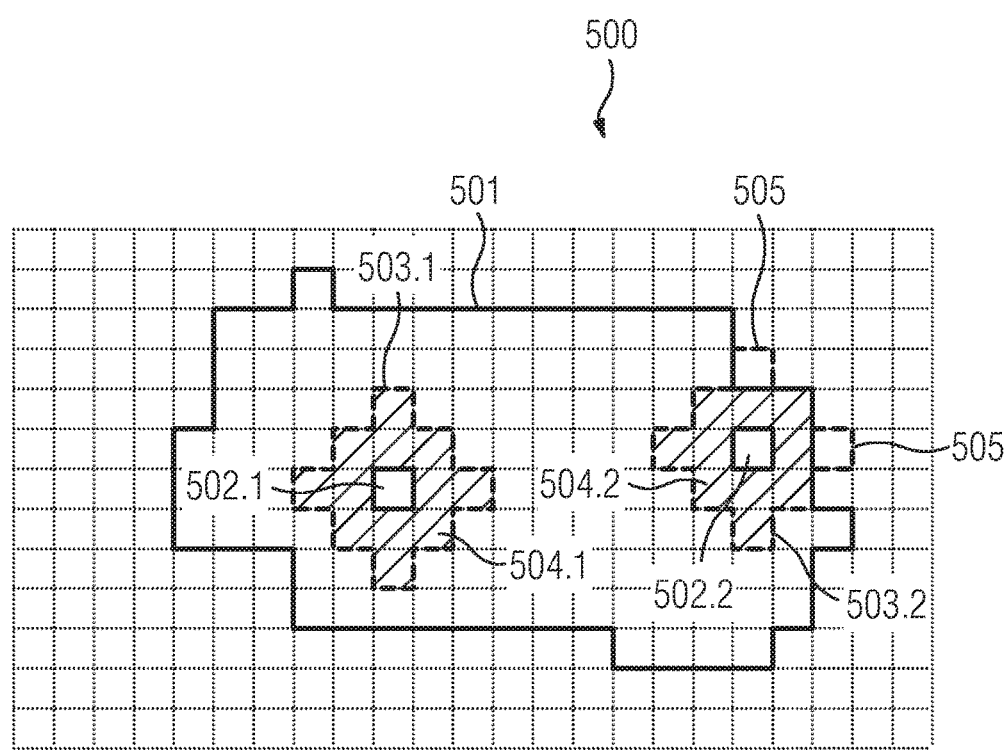
FIG. 5 shows a tumor region.

FIG. 5 shows an image data set 500 with a tumor region 501. The tumor region 501 comprises a plurality of image points 502.1, 502.2 of the image data set 500. Furthermore, FIG. 5 shows surrounding areas 503.1, 503.2 around image points 502.1, 502.2 in the tumor region 501. The texture parameter of an image point 502.1, 502.2 is based on the first intensity values in the section 504.1, 504.2 of the surrounding area 503.1, 503.2 around the image point 502.1, 502.2 with the tumor region 501. In the example embodiment depicted, a surrounding area 503.1, 503.2 around an image point 502.1, 502.2 comprises all image points of the image data set 500 with a maximum distance of 2 pixels to the image point 502.1, 502.2. Herein, the distance is formed by the sum of the vertical and horizontal difference. If a surrounding area 503.2 is located at the edge of the tumor region 501, the texture parameter of the image point 502.2 is not based on the intensity values 505 outside the tumor region 501. However, alternatively, it is also possible, not to restrict the texture parameter to intensity values of the tumor region 501, but to calculate the texture parameter of an image point 502.1, 502.2 by way of all intensity values in the surrounding area 503.1, 503.2 around the image point 502.1, 502.2.

The following describes variables, which a texture parameter can comprise and which are based on a spatial distribution of intensity values. A texture parameter can be a texture parameter assigned to an image point 502.1, 502.2 in the tumor region 501 or a training texture parameter assigned to a training image point in the training tumor region. The spatial distribution of intensity values can be the spatial distribution of first intensity values of the image data set and/or the spatial distribution of second intensity values of the image data set and/or the spatial distribution of first and/or second training intensity values of the first training image data set 421.1, 421.2 and/or the spatial distribution of first and/or second training intensity values of the second training image data set 422.1, 422.2.

A texture parameter can comprise the mean value of the first intensity values and/or the second intensity values. A texture parameter can also comprise the minimum and/or maximum of the first intensity values and/or the second intensity values.

A texture parameter furthermore enables a moment and/or a central moment of a histogram of the first intensity values and/or the second intensity values. A central moment can in particular be the variance, the standard deviation, the skewness (an English technical term; a German translation is "Schiefe") and/or the kurtosis (an English technical term; a German translation is "Wölbung") of the histogram of the first intensity values and/or the second intensity values.

The texture parameter can furthermore comprise the entropy S of the first intensity values. The entropy S is defined as $$S = -\sum_i p(i) \cdot \log p(i)$$

wherein the sum is a sum covering all possible intensity values i and wherein p(i) is the relative frequency of the intensity value i.

A texture parameter can in particular also comprise a variable, which is dependent upon one of the graytone matrices. In particular, a texture parameter can also comprise a plurality of variables, which are dependent on one of the graytone matrices. In particular, a texture parameter can comprise the contrast C(G), the correlation Cor(G), the energy E(G) and/or the homogeneity H(G) of one of the graytone matrices G. These variables are calculated as $$C(G) = \sum_{mn} (m-n)^2 \cdot G_{mn}$$

$$\text{Cor}(G) = \sum_{mn} \frac{(m-\mu_m)(n-\mu_n)}{\sigma_m \sigma_n} G_{mn}$$

$$E(G) = \sum_{mn} (G_{mn})^2$$

$$H(G) = \sum_{mn} \frac{1}{1+|m-n|} G_{mn}$$

Herein $\mu_m$ designates the mean value and $\sigma_m$ the standard deviation of the column-wise sums of the graytone matrix G, furthermore $\mu_n$ designates the mean value and $\sigma_n$ the standard deviation of the row-wise sums of the graytone matrix G. The contrast C(G) of a graytone matrix is also designated as variance or inertia (an English technical term; a German translation is "Trägheit") of the graytone matrix. The energy E(G) of a graytone matrix is also designated as uniformity or angular second moment (an English technical term; a German translation is "zweites Winkeldrehmoment").

A texture parameter can in particular also comprise a variable, which is dependent upon one of the run-length matrices. In particular, a texture parameter can also comprise a plurality of variables, which are dependent upon one of the run-length matrices. In particular, a texture parameter can comprise the "short run emphasis" SRE (a German translation is "Kurzlängenbetonung") or the "long run emphasis" LRE (a German translation is "Langlängenbetonung"):

$$SRE(L) = \sum_{m,r} \frac{L_{mr}}{r^2} \Big/ \sum_{m,r} L_{mr}$$

$$LRE(L) = \sum_{m,r} r^2 L_{mr} \Big/ \sum_{m,r} L_{mr}$$

Furthermore, a texture parameter can in particular comprise "gray level nonuniformity" GLN (a German translation is "Grauwertungleichmäßigkeit" or "run length nonuniformity" RLN (a German translation is "Lauflängenungleichmäßigkeit):

$$GLN(L) = \sum_m \left(\sum_r L_{mr}\right)^2 \Big/ \sum_{m,r} L_{mr}$$

$$RLN(L) = \sum_r \left(\sum_m L_{mr}\right)^2 \Big/ \sum_{m,r} L_{mr}$$

A texture parameter can furthermore comprise one or more variables, which are dependent upon one of the "neighborhood graytone difference matrices" (a German translation is "Nachbarschafts-Grauwertdifferenz-Matrix). A texture parameter can also comprise coarseness (an English technical term; a German translation is "Grobheit") as a measure of the edge density, furthermore a texture parameter can comprise the "busyness" (a German translation is "Geschäftigkeit") or the heterogeneity as a measure of the number of edges.

A texture parameter can furthermore comprise one or more variables, which are dependent on a convolution with a convolution mask, in particular on a convolution with one or more masks of Law's texture energy measure (an English technical term; a German translation is "Lawsches Textur-Energie-Maß").

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining a biopsy position, comprising:
    receiving an image data set of an examination volume via an interface, the examination volume including a tumor;
    segmenting a tumor region in the image data set via a computing unit;
    determining a texture distribution of the tumor region via the computing unit, the texture distribution assigning a respective texture parameter to respective image points in the tumor region and each of the respective texture parameters being based on a spatial distribution of first intensity values of the image data set; and
    determining, via the computing unit, a biopsy position within the tumor region by applying an optimized position-determining algorithm to the texture distribution, the optimized position-determining algorithm being based on training texture distributions and first training positions, respective ones of the first training positions being assigned to respective ones of the training texture distributions.

2. The method of claim 1, wherein each of the respective texture parameters is based on the spatial distribution of the first intensity values in a surrounding area around the respective image point.

3. The method of claim 2, wherein each of the respective surrounding areas around one of the respective image points includes a same geometric shape and a same orientation, and wherein, with each of the respective surrounding areas, one of the respective image points has a same position relative to the one of the respective image points.

4. The method of claim 1, wherein each of the respective texture parameters is based at least on at least one of
    a histogram,
    a graytone matrix,
    a run-length matrix,
    a convolution with a convolution window, an autocorrelation, and
    a transform of the first intensity values of the image data set.

5. The method of claim 1, wherein each of the respective texture parameters comprises at least one scaling-invariant variable, wherein the at least one scaling-invariant variable is based on the first intensity values of the image data set in the tumor region, and wherein, on statistical average, the at least one scaling-invariant variable is independent of the spatial resolution of the image data set.

6. The method of claim 1, wherein each of the respective texture parameters is a measure for at least one of shape and structure of the tumor.

7. The method of claim 1, wherein each of the texture parameters is furthermore based on a spatial distribution of second intensity values of the image data set.

8. The method as claimed in claim 7, wherein the first and the second intensity values are both computed tomography Hounsfield intensity values, wherein the first intensity values were acquired with a first X-ray energy, wherein the second intensity values were acquired with a second X-ray energy, and wherein the first X-ray energy is relatively greater than the second X-ray energy.

9. The method of claim 7, wherein the first intensity values are computed tomography Hounsfield intensity values, wherein the second intensity values are positron-emission-tomography intensity values and wherein positron-emission-tomography intensity values are a measure for a number of emitted positrons.

10. A method for optimizing a position-determining algorithm, comprising:
receiving, via a training interface, a first training image data set and a second training image data set of a training tumor region;
determining, via a training computing unit, a training texture distribution of the training tumor region via a training computing unit, the training texture distribution assigning a respective training texture parameter to respective first training image points of the first training image data set, each of the respective training texture parameters being based on a spatial distribution of first training intensity values of the first training image data set;
determining, via the training computing unit, a first training position in the first training image data set based on a growth rate in the training tumor region, the growth rate being based on the second training image data set;
receiving a position-determining algorithm via the training interface, the position-determining algorithm being based on a plurality of algorithm parameters;
determining, via the training computing unit, a second training position by applying the position-determining algorithm to the training texture distribution; and
optimizing, via the training computing unit, the position-determining algorithm by adjusting the algorithm parameters based on a comparison of the first training position with the second training position.

11. The method of claim 10, wherein the second training image data set is a positron-emission training image data set and wherein the growth rate in a second training image data point of the second training image data set is directly proportional to a number of detected electron-positron pairs in the second training image data point.

12. The method of claim 10, wherein an acquisition time point of the first training image data set is chronologically relatively later than an acquisition time point of the second training image data set, and wherein the growth rate is determined based on a comparison of the first training image data set and the second training image data set.

13. The method of claim 10, wherein the position-determining algorithm is an artificial neural network or a Bayesian network and wherein the algorithm parameters are the edge weights of the artificial neural network or the Bayesian network.

14. A position-determining unit for determining a biopsy position, comprising:
an interface, embodied to receive an image data set of an examination volume, the examination volume including a tumor;
a computing unit, embodied to
segment a tumor region in the image data set,
determine a texture distribution of the tumor region, the texture distribution assigning a respective texture parameter to respective image points in the tumor region, each of the respective texture parameters being based on a spatial distribution of first intensity values of the image data set,
determine a biopsy position within the tumor region by applying an optimized position-determining algorithm to the texture distribution, the optimized position-determining algorithm being based on training texture distributions and first training positions, and one of the training positions being assigned to each of the respective training texture distributions.

15. The position-determining unit of claim 14, wherein each of the respective surrounding areas around one of the respective image points includes a same geometric shape and a same orientation, and wherein, with each of the respective surrounding areas, one of the respective image points has a same position relative to the one of the respective image points.

16. An imaging medical device embodied to determine a biopsy position, comprising:
the position-determining unit of claim 14.

17. A non-transitory computer-program product including a computer program, directly loadable into a memory of a position-determining unit, the computer program including program sections for carrying out the method of claim 1 when the program sections are executed by the position-determining unit.

18. A non-transitory computer-readable storage medium storing program sections, readable and executable by a position-determining unit, to carry out the method of claim 1 when the program sections are executed by the position-determining unit.

19. A non-transitory computer-program product including a computer program, including the optimized position-determining algorithm of claim 10, directly loadable into a memory of a position-determining unit.

20. A non-transitory computer-readable storage medium storing program sections, readable and executable by a position-determining unit, the computer program including the optimized position-determining algorithm of claim 10.

21. The method of claim 2, wherein each of the respective texture parameters is based at least on at least one of
a histogram,
a graytone matrix,
a run-length matrix,
a convolution with a convolution window, an autocorrelation, and
a transform of the first intensity values of the image data set.

22. The method of claim 2, wherein each of the respective texture parameters comprises at least one scaling-invariant variable, wherein the at least one scaling-invariant variable is based on the first intensity values of the image data set in the tumor region, and wherein, on statistical average, the at least one scaling-invariant variable is independent of the spatial resolution of the image data set.

23. The method of claim 2, wherein each of the respective texture parameters is a measure for at least one of shape and structure of the tumor.

24. The method of claim 11, wherein the position-determining algorithm is an artificial neural network or a Bayesian network and wherein the algorithm parameters are the edge weights of the artificial neural network or the Bayesian network.

25. The method of claim 12, wherein the position-determining algorithm is an artificial neural network or a Bayesian network and wherein the algorithm parameters are the edge weights of the artificial neural network or the Bayesian network.

26. An imaging medical device embodied to determine a biopsy position, comprising:

the position-determining unit of claim 15.

27. A non-transitory computer-program product including a computer program, directly loadable into a memory of a position-determining unit, the computer program including program sections for carrying out the method of claim 10 when the program sections are executed by the position-determining unit.

28. A non-transitory computer-readable storage medium storing program sections, readable and executable by a position-determining unit, to carry out the method of claim 10 when the program sections are executed by the position-determining unit.

\* \* \* \* \*